(12) United States Patent
Bae et al.

(10) Patent No.: US 7,070,680 B2
(45) Date of Patent: Jul. 4, 2006

(54) BIOSENSOR

(75) Inventors: Byung-Woo Bae, Kyunggi-Do (KR); Heon-Kwon Lee, Kyunggi-Do (KR); Sung-Dong Lee, Seoul (KR); Mi-Joong Kwon, Seoul (KR)

(73) Assignee: Infopia Co., Ltd., Anyang-si (KR)

( * ) Notice: Subject to any disclaimer, the term of this patent is extended or adjusted under 35 U.S.C. 154(b) by 0 days.

(21) Appl. No.: 10/514,236

(22) PCT Filed: Oct. 4, 2002

(86) PCT No.: PCT/KR02/01854

§ 371 (c)(1),
(2), (4) Date: Nov. 19, 2004

(87) PCT Pub. No.: WO03/097866

PCT Pub. Date: Nov. 27, 2003

(65) Prior Publication Data

US 2005/0161323 A1 Jul. 28, 2005

(30) Foreign Application Priority Data

May 20, 2002 (KR) .................. 10-2002-0027971

(51) Int. Cl.
*G01N 27/327* (2006.01)
(52) U.S. Cl. .............................. 204/403.04; 204/403.14
(58) Field of Classification Search ................ 204/403.01–403.14
See application file for complete search history.

(56) References Cited

U.S. PATENT DOCUMENTS

| 5,958,199 | A | 9/1999 | Miyamoto et al. |
| 5,985,116 | A | 11/1999 | Ikeda et al. |
| 6,004,441 | A | 12/1999 | Fujiwara et al. |
| 6,059,946 | A | 5/2000 | Yukawa et al. |
| 6,077,408 | A | 6/2000 | Miyamoto et al. |
| 6,212,417 | B1 | 4/2001 | Ikeda et al. |
| 6,458,258 | B1 | 10/2002 | Taniike et al. |
| 6,787,013 | B1 * | 9/2004 | Chang et al. ............ 204/412 |
| 2004/0146958 | A1 | 7/2004 | Bae et al. |

* cited by examiner

*Primary Examiner*—Alex Noguerola
(74) *Attorney, Agent, or Firm*—Greenblum & Bernstein, P.L.C.

(57) ABSTRACT

A biosensor for quantifying a specific substance contained in a biological sample includes an electrically insulating base plate, a plurality of lead terminals formed on the base plate, a plurality of lead wires connected to the lead terminals, respectively, an electrode system including two working electrodes and one reference electrode connected to the lead wires, respectively, an insulating layer that insulates the electrodes, an enzyme reaction layer formed on the insulating layer and the electrodes, a spacer formed on the enzyme reaction layer so as to ensure a sufficient space that receives a sample, and a cover formed on the spacer. Further, the spacer has a sample introduction port opened at one side of the spacer, the cover has at least one slit for venting air existing in a sample receiving space defined by the spacer and the cover, and the slit extends to above the electrodes from one end of the cover.

12 Claims, 8 Drawing Sheets

Fig.1

Prior Art

Fig.2

Prior Art

BIOSENSOR

This application claims priority under 35 U.S.C. § 371 from PCT/KR02/01854, filed on Oct. 4, 2002 and under 35 U.S.C. § 119(a–d) from Korean patent application KR 2002/27971, filed on May 20, 2002.

TECHNICAL FIELD

The present invention relates to a sensor, and more specifically to a biosensor for quantifying a specific substance contained in a biological sample.

BACKGROUND ART

Generally, a biosensor comprises an electrically insulating base plate, an electrode system including a plurality of electrodes and formed on the electrically insulating base plate using a screen printing method, and an enzyme reaction layer including a hydrophilic polymer, oxidoreductase and an electron acceptor and formed on the electrode system. When a sample liquid containing a substrate is dropped on the enzyme reaction layer of the biosensor, the enzyme reaction layer is dissolved to allow the substrate and enzyme to react with each other. At a result, the substrate is oxidized, and then the electron acceptor is reduced. After such an enzyme reaction finishes, the concentration of the substrate in the sample liquid is determined from an oxidation current obtained by electrochemically oxidizing the reduced electron acceptor.

Figure 1:
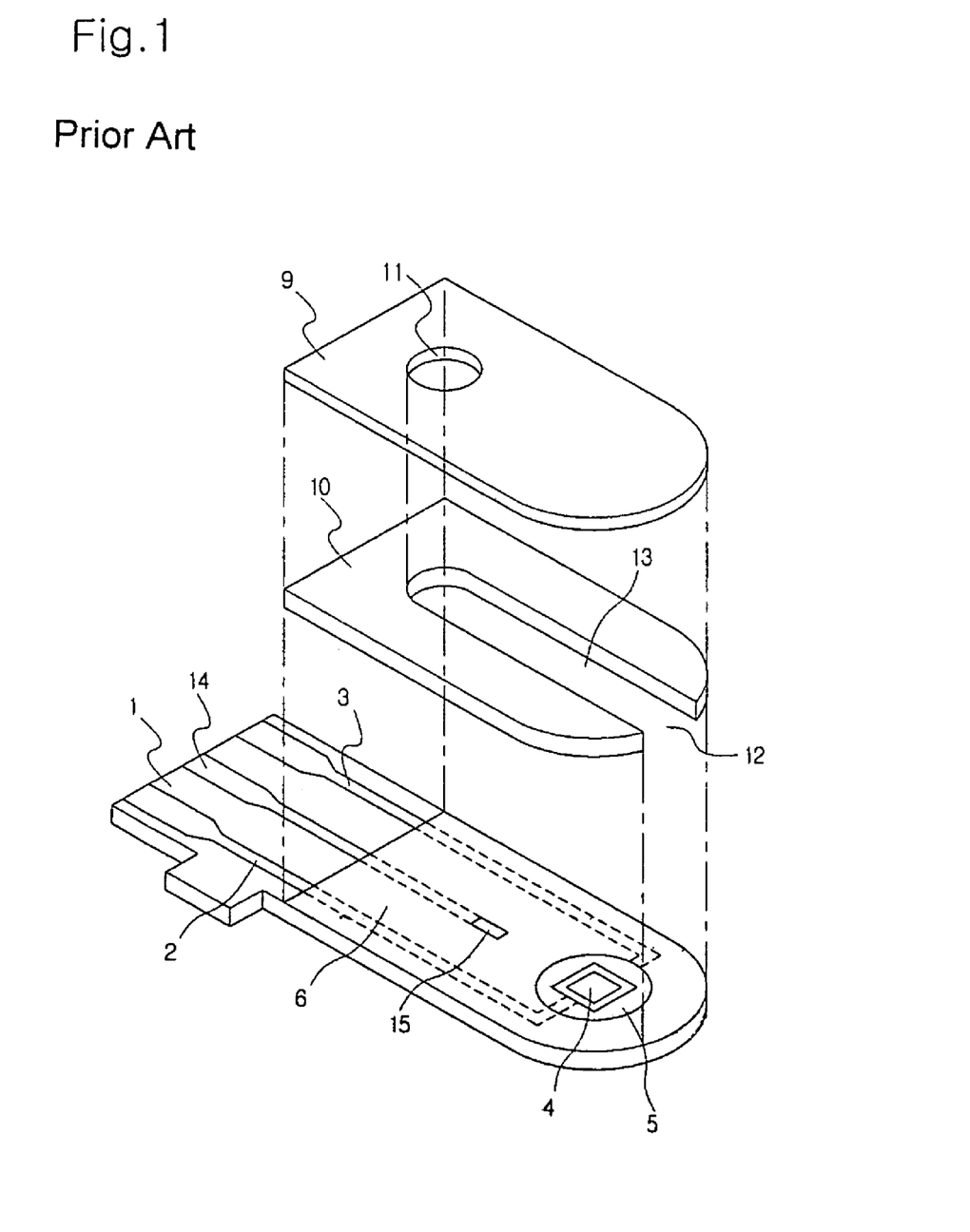
FIG. 1 is an exploded perspective view of a conventional biosensor in which a reaction layer is omitted.
Figure 2:
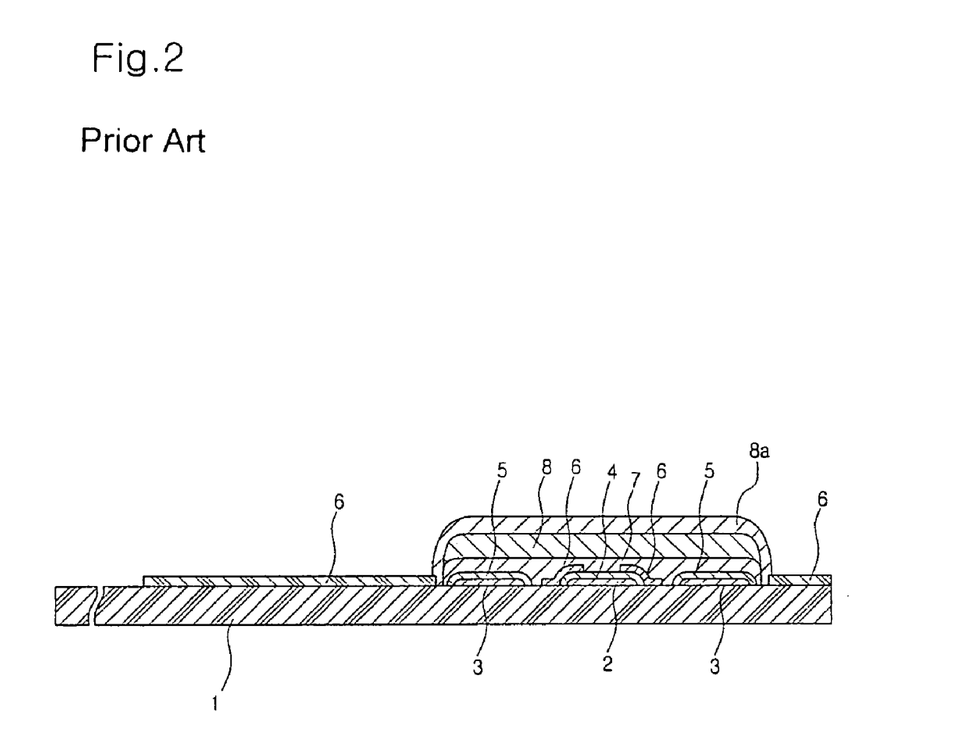
FIG. 2 is a longitudinal sectional view of the biosensor shown in FIG. 1.

As a biosensor for quantifying a specific substance contained in a biological sample using an electrochemical manner, a glucose sensor is known. FIGS. 1 and 2 show a structure of the glucose sensor.

FIG. 1 is an exploded perspective view of a conventional biosensor in which a reaction layer is omitted. FIG. 2 is a longitudinal sectional view of the biosensor shown in FIG. 1.

Referring to FIG. 1, silver paste is screen-printed on an electrically insulating base plate 1 to form leads 2 and 3 on a base plate 1. Conductive carbon paste containing a resin binder is then printed on the base plate 1 to form an operating electrode 4 on the base plate 1. The operating electrode 4 is contacted with the lead 2. Electrically insulating paste is then printed on the base plate 1 to form an insulating layer 6. The insulating layer 6 covers all portions except the operating electrode 4 so that the exposed area of the operating electrode 4 is maintained to be constant. Conductive carbon paste containing the resin binder is printed on the base plate 1 to come into contact with the lead 3 and thus to form a ring-shaped counter electrode 5. Subsequently, on or near an electrode system including the operating electrode and the counter electrode, a reaction layer is formed.

The electrically insulating base plate 1 having the reaction layer and a cover 9 having an air hole 11 are bonded to each other via a spacer 10, along dashed dot lines marked in FIG. 1, to manufacture a biosensor. A slit 13 is formed at the spacer 10 to provide a sample supplying path between the base plate and the cover. Referring to a longitudinal sectional view of the biosensor having the above-mentioned structure, a hydrophilic polymer layer 7 is disposed at the electrically insulating base plate 1 having the electrode system, and a reaction layer 8 including enzymes and electron acceptors and a lecithin layer 8a are disposed on the hydrophilic polymer layer 7 in this order.

When a biological sample is contacted with an introduction port 12 of the biosensor having the above-mentioned structure, the biological sample fills the slit 13 acting as a sample receiving space, and at the same time air in the sample receiving space is vented through an air hole 11 formed at the cover 9.

However, since the air hole 11 is formed at the upper part of the biosensor, the biosensor is disadvantageous in terms of its handling due to measurement errors caused by frequent contact with the air hole 11 when using the biosensor. Considering the fact that the reaction progresses immediately after the sample comes into contact with the reaction layer, it is important to rapidly absorb the sample irrespective of viscosity of the sample. However, in the biosensor having the above-mentioned structure, since the air hole 11 for venting air is arranged at the rear side of a sample introduction passage, rapid absorption of the sample is limited. Such limited absorption of the sample causes measurement errors in biosensors that initiate the measurement after checking whether or not the sample is completely introduced.

DISCLOSURE OF THE INVENTION

Therefore, the present invention has been made in view of the above problems, and it is an object of the present invention to provide a biosensor capable of rapidly inducing absorption of a biological sample, thereby minimizing measurement errors caused by the biosensor.

It is another object of the present invention to provide a biosensor which can provide simplicity and convenience in handling the biosensor and accurately measure a reactive substance contained in a sample using two working electrodes and one reference electrode.

To achieve the above objects, there is provided a biosensor comprising: an electrically insulating base plate 20; a plurality of lead terminals 32 formed on the base plate 20; a plurality of lead wires 31 connected to the lead terminals 32, respectively; an electrode system 40 including two working electrodes 42 and 43 and one reference electrode 41 connected to the lead wires 31, respectively; an insulating layer 50 for insulating the electrodes 41, 42 and 43; an enzyme reaction layer 80 formed on the insulating layer 50 and the electrodes 41, 42 and 43; a spacer 60 formed on the enzyme reaction layer 80 so as to ensure a sufficient space for receiving a sample; and a cover 70 formed on the spacer 60, wherein the spacer 60 has a sample introduction port 61 formed at one side of the spacer 60, and the cover 70 has at least one slit 71 for venting air existing in a sample receiving space 62 defined by the spacer 60 and the cover 70, the slit 71 extending to above the electrodes 41, 42 and 43 from one end of the cover 70.

In the biosensor according to the embodiment of the present invention, since the sample receiving space 62 is opened through the slit 71, a biological sample is rapidly introduced into the biosensor by virtue of maximized capillary effect.

In accordance with one aspect of the present invention, there is provided a biosensor further including a curved groove 72 formed at one end of the cover 70 toward the electrodes 41, 42 and 43, the slit 71 being formed from a certain position of the curved groove 72 with a predetermined length. The biosensor having the above-mentioned structure can collect a quantity of biological sample in the curved groove 72.

In accordance with the embodiment of the biosensor according to the present invention, the respective working electrodes 42 and 43 have the same electrical resistance and area, and the reference electrode 41 is spaced at the same distance from the respective working electrodes 42 and 43 and has an area above 1.5 times larger than the working electrodes 42 and 43.

BRIEF DESCRIPTION OF THE DRAWINGS

The above and other objects, features and other advantages of the present invention will be more clearly understood from the following detailed description taken in conjunction with the accompanying drawing, in which.

BEST MODE FOR CARRYING OUT THE INVENTION

Hereinafter, the present invention will be explained in more detail through preferred embodiments, with reference to the accompanying drawings in such a manner that it may easily be carried out by a person having ordinary skill in the art.

Figure 3A:
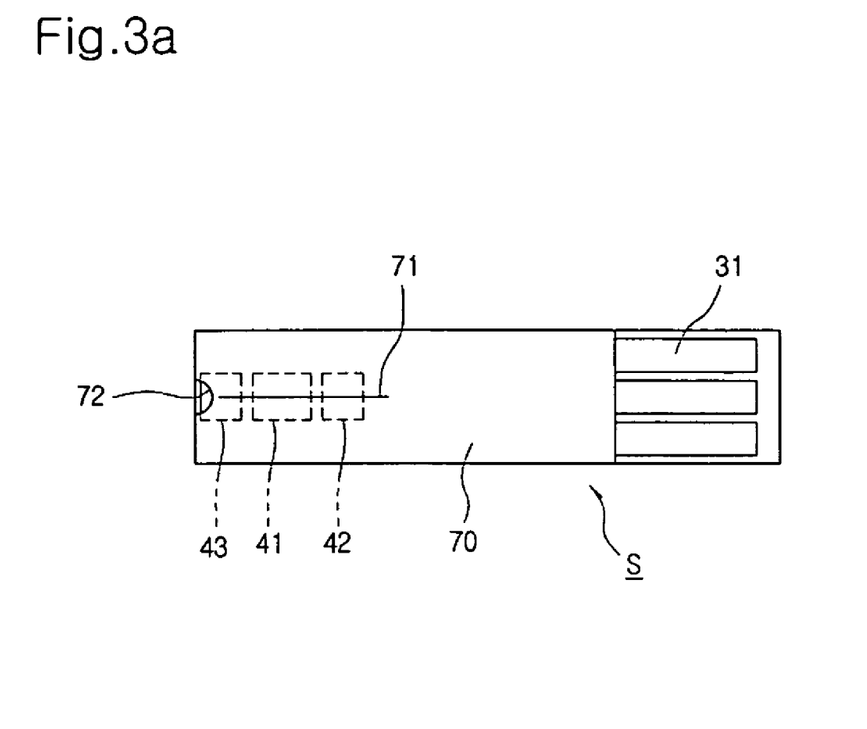
FIGS. 3*a* and 3*b* are a top view and a back view of a biosensor according to an embodiment of the present invention, respectively.
Figure 3B:
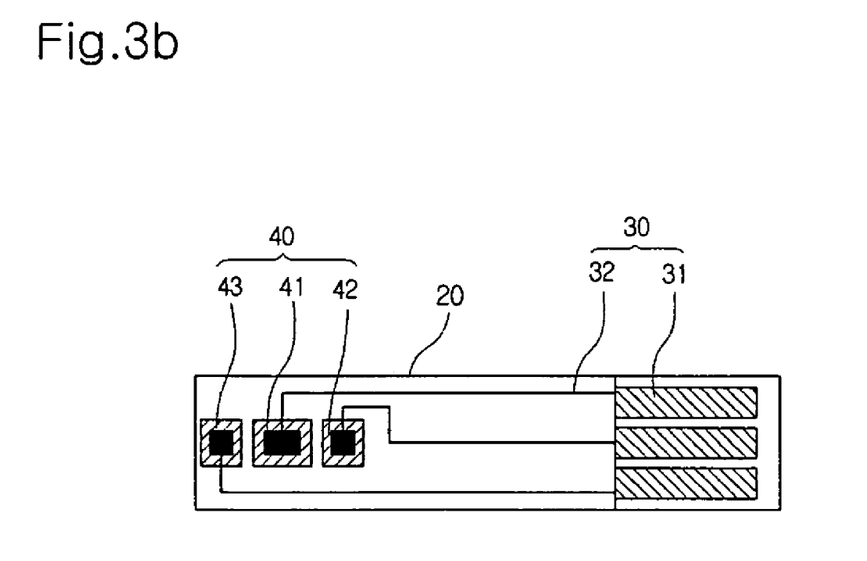

FIGS. 3*a* and 3*b* are a top view and a back view of a biosensor according to an embodiment of the present invention, respectively.

Referring to FIG. 3*a*, a plurality of lead terminals 31 corresponding to the number of electrodes are formed at one end of an electrically insulating base plate 20. As shown in FIG. 3*b*, the lead terminals 31 are connected to electrodes 41, 42 and 43, respectively, formed at the other end of the electrically insulating base plate 20 through respective lead wires 32. As shown in FIG. 3*a*, a slit 71 is formed at a cover 70 of the biosensor S according to the embodiment of the present invention, and extends from a curved groove 72 formed at one end of the cover 70 toward the electrodes 41, 42 and 43 to at least above the electrodes 41, 42 and 43. The slit 71, which will be discussed below, acts as an air-vent when a biological sample is introduced by the capillary phenomenon.

The electrically insulating base plate 20 may be made of a non-conductive material such as polyethylene terephthalate, polyvinyl chloride resin, polycarbonate resin, etc. A lead section 30 including the lead wires 32 and the lead terminals 31 may be formed in accordance with a common method such as screen printing. In the embodiment of the present invention, the lead section 30 was formed by screen-printing a silver ink or a mixed ink of silver and silver chloride on the base plate 20.

The structure of the biosensor S will now be explained in more detail with reference to the exploded perspective view and cross-sectional view of FIGS. 3*a* and 3*b*.

Figure 4:
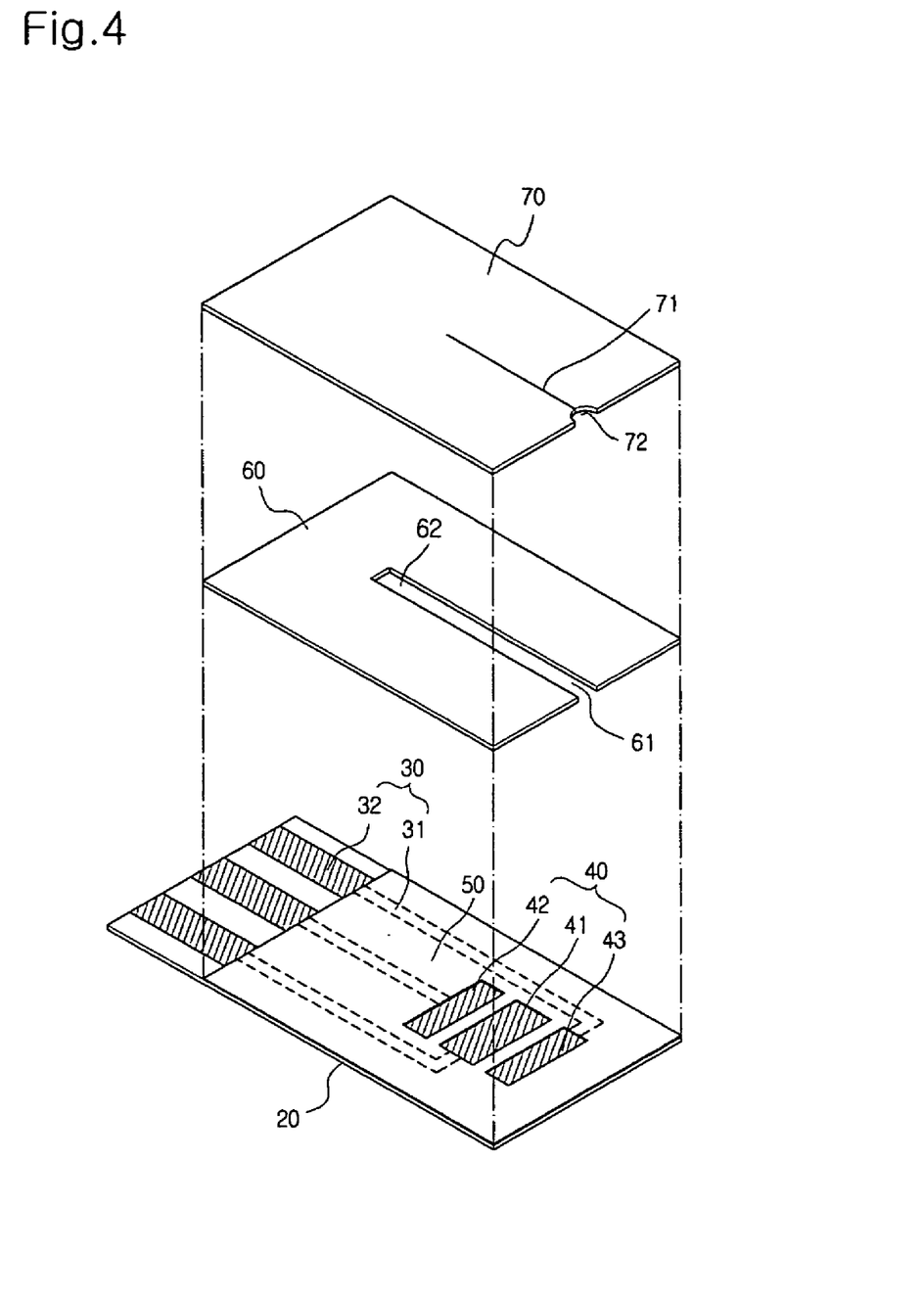
FIG. 4 is an exploded perspective view of a biosensor according to an embodiment of the present invention.
Figure 5:
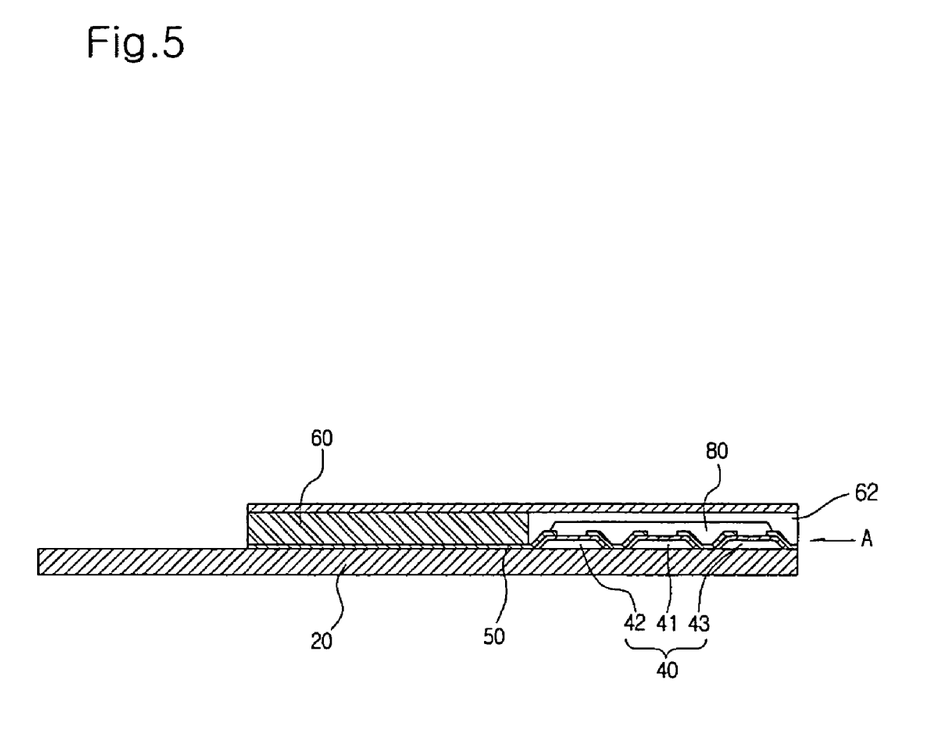
FIG. 5 is a cross-sectional view of a biosensor according to an embodiment of the present invention.

FIG. 4 is an exploded perspective view of the biosensor S according to the embodiment of the present invention, and FIG. 5 is a cross-sectional view of the biosensor according to the embodiment of the present invention.

Referring to FIG. 4, the biosensor S according to the embodiment of the present invention comprises the electrically insulating base plate 20, the base plate 20 having three lead terminals 32 formed on one end of the base plate 20, the lead terminals 32 being connected to three electrodes 41, 42 and 43, respectively, through the lead wires 31. In the electrodes 41, 42 and 43, a reference numeral 41 denotes a reference electrode, and reference numerals 42 and 43 denote working electrodes. These electrodes act to measure the amount of current generated during oxidation and reduction of an electron acceptor included in an enzyme reaction layer 80, which will be discussed below. The reference electrode 41 is arranged between the respective working electrodes 42 and 43. This electrode arrangement makes it possible to measure the amounts of current in the reference electrode 41 and the respective working electrodes 42 and 43. That is, the biosensor according to the embodiment of the present invention measures the amounts of current between the first working electrode 43 and the reference electrode 41, and the second working electrode 42 and the reference electrode 41, compares the measured values and determines errors generated in the manufacture of the biosensor and the reaction with a substrate, thereby quantitatively obtaining the concentration of the substrate contained in the biological sample with an increased accuracy.

In accordance with the embodiment of the biosensor according to the present invention, in order to measure the amounts of current in the reference electrode 41 and the respective working electrodes 42 and 43 under the same electrochemical conditions, the respective working electrodes 42 and 43 must have the same electrical resistance and area, and the reference electrode 41 must be spaced at the same distance from the respective working electrodes 42 and 43. In addition, the area of the reference electrode (41) is preferably more than 1.5 times larger than that of the working electrodes 42 and 43. Since the amounts of current generated in the reference electrode 41 and the respective working electrodes 42 and 43 is proportional to the reactive area of the electrodes, the relatively large area of the reference electrode 41 can reduce measurement errors between the reference electrode 41 and the respective working electrodes 42 and 43. The reference electrode 41 and the working electrodes 42 and 43 are collectively referred to as "an electrode system 40". The electrode system 40 can be formed by a screen printing method using a conductive carbon ink.

In order to insulate the electrodes 41, 42 and 43, an insulating material is partially coated on the electrodes 41, 42 and 43 except the upper portions of the electrodes 41, 42 and 43 to form an insulating layer 50, as shown in FIG. 5. As the insulating material, a non-conductive ink for screen printing or an ink for insulation can be used. The enzyme reaction layer 80 is formed on both the exposed portions of the electrodes 41, 42 and 43 and the insulating layer 50. The enzyme reaction layer 80 includes an enzyme reactive with the introduced biological sample, and an electron acceptor.

The enzyme reaction layer 80 must include an enzyme reactive with a substrate to be detected. That is, the enzyme reaction layer 80 can include different enzymes depending on the application of the biosensor. Examples of the enzymes and substrates are shown in Table 1 below. As shown in Table 1, when the biosensor according to the embodiment of the present invention is a glucose sensor, the enzyme reaction layer 80 includes glucose oxidase. When a blood sample as the biological sample is introduced into the enzyme reaction layer 80 of the sensor, glucose in blood is oxidized by glucose oxidase, after which the glucose oxidase is reduced. Herein, the electron acceptor included in the enzyme reaction layer 80 oxidizes the glucose oxidase and then itself is reduced. The reduced electron acceptor loses its electrons on the surface of the electrode, to which a constant voltage is applied, and then is electrochemically reoxidized. Since the concentration of glucose in the blood sample is proportional to the amount of current generated when the electron acceptor is oxidized, the concentration of glucose in the blood sample can be measured by measuring the amount of current through the lead terminals 32.

TABLE 1

| Substrate | Enzymes |
|---|---|
| Glucose | Glucose oxidase |
| Cholesterol | Cholesterol esterase |
|  | Cholesterol oxidase |
|  | Peroxidase |
| Creatinine | Creatininase |
|  | Creatinase |
|  | Sarcosine oxidase |
| Lactate | Lactate oxidase |

On the other hand, in accordance with the biosensor S according to the embodiment of the present invention, a spacer 60 having a sample introduction port 61 for forming a sample receiving space is formed on the enzyme reaction layer 80, and is sandwiched between the base plate 20 and the cover 70. In order to form the sample receiving space 62 between the cover 70 and the enzyme reaction layer 80 when the cover 70 and the spacer 60 are bonded to each other, the spacer 60 must be higher than the enzyme reaction layer 80 formed on the base plate 20. The spacer 60 can be made of resin. In the embodiment of the present invention, a double-sided tape made of resin was used as the spacer 60.

In accordance with the biosensor S according to the embodiment of the present invention, the cover 70 is bonded to the spacer 60. At this time, in order to vent air existing in the sample receiving space 62 between the spacer 60 and the cover 70, the slit 71 is formed at the cover 70. For stable introduction of the biological sample into above the electrode 42, the slit 71 extends to at least above the electrodes 41, 42 and 43 with a predetermined length.

In the biosensor S as shown in FIG. 5, the spacer 60 is bonded to the upper side of the insulating layer 50. However, the spacer 60 can be directly bonded to the base plate 20 instead of the insulating layer 50.

Figure 6:
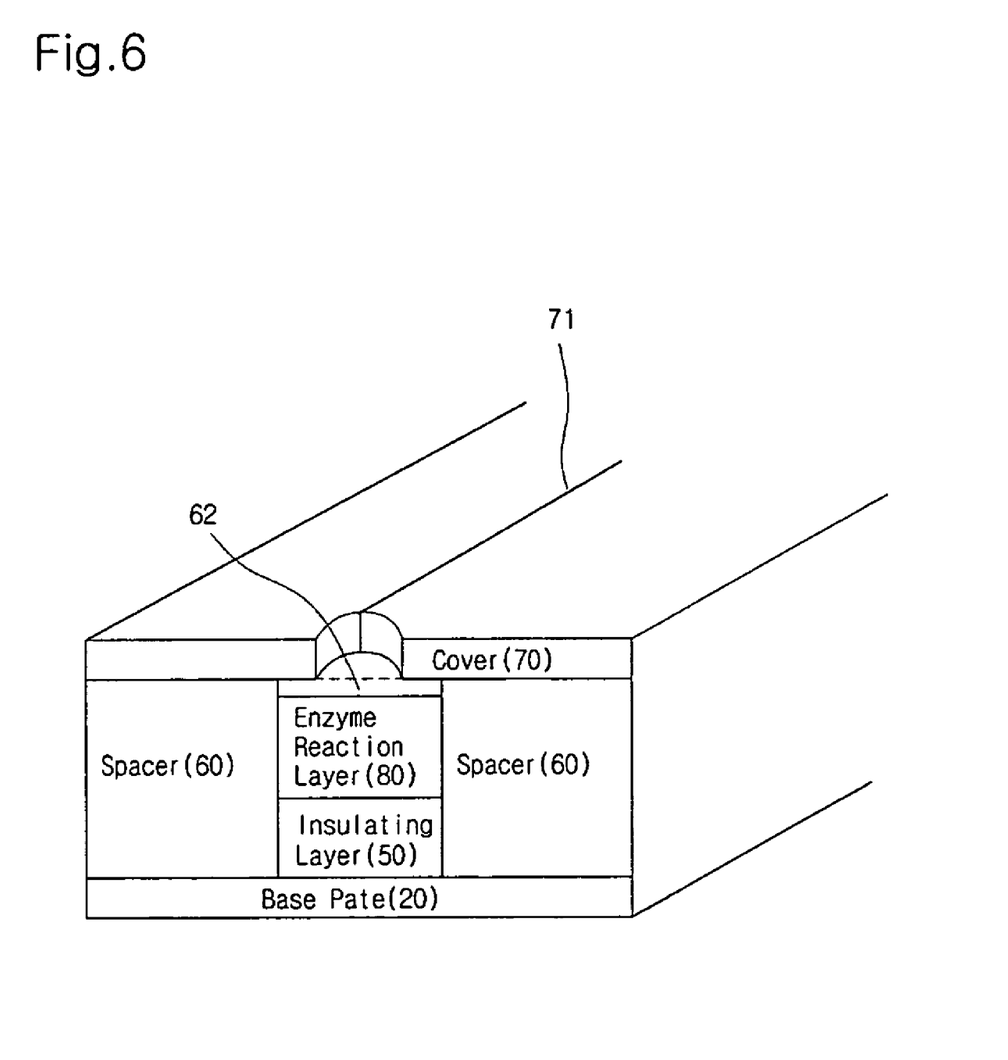
FIG. 6 is a front view of the biosensor when viewed from a direction A (shown by an arrow) in FIG. 5.

FIG. 6 is a front view of the biosensor when viewed from a direction A in FIG. 5.

Referring to FIG. 6, the base plate 20 is placed at the bottom of the biosensor S according to the embodiment of the present invention, the insulating layer 50 insulates the electrodes 41, 42 and 43 formed on the base plate 20, and the enzyme reaction layer 80 is formed on the insulating layer 50. Since the spacer 60 is higher than the enzyme reaction layer 80 and is placed around the electrodes 41, 42 and 43, the sample receiving space 62 is formed between the cover 70 and the enzyme reaction layer 80. Since the slit 71 formed at the cover 70 acts as an air-vent, the biological sample is introduced into the sample receiving space 62 by virtue of capillary phenomenon.

FIGS. 7a to 7e are diagrams showing various electrode arrangements and positions of the slit 71 for venting air in the biosensor S according to the embodiment of the present invention.

Figure 7A:
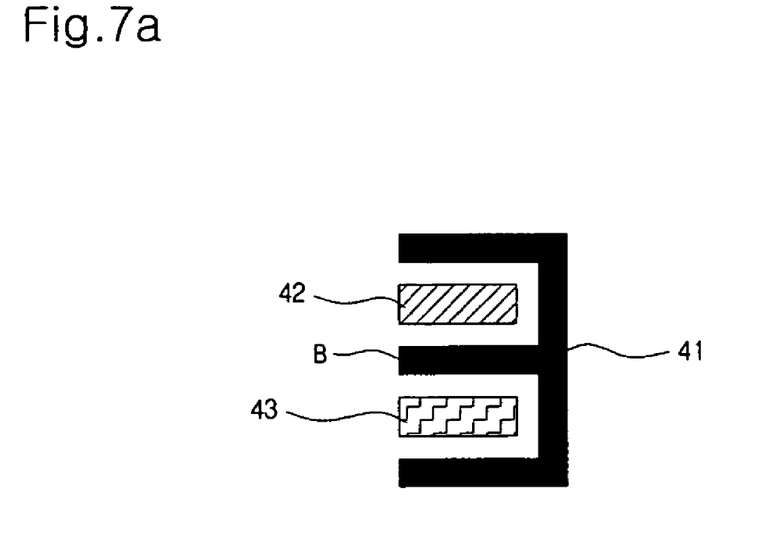
FIGS. 7*a* to 7*e* are diagrams showing various electrode arrangements and positions of the slit for venting air in a biosensor according to an embodiment of the present invention.

In the biosensor S according to the embodiment of the present invention, the electrode system 40 including the reference electrode 41 and the working electrodes 42 and 43 can be formed as shown in FIG. 7a. That is, the reference electrode 41 has an E-shape, and the respective working electrodes 42 and 43 can be arranged at the upper and lower portions of a horizontal axis B, which is formed at the center of the reference electrode 41. In this case, the respective working electrodes 42 and 43 must also have the same electrical resistance and area, and the reference electrode 41 must be spaced at the same distance from the respective working electrodes 42 and 43.

Figure 7B:
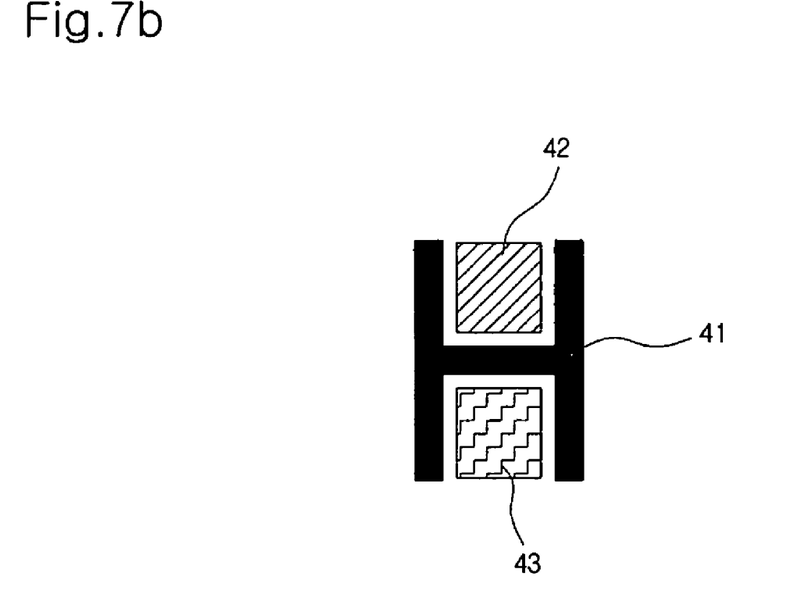

In accordance with another embodiment of the present invention, the electrode system 40 can be formed as shown in FIG. 7b. That is, when the sample receiving space 62 is placed in a vertical direction, the reference electrode 41 has an H-shape, and the respective working electrodes 42 and 43 can be arranged at the upper and lower portions of a horizontal axis of the reference electrode 41. Also, the respective working electrodes 42 and 43 must have the same electrical resistance and area, and the reference electrode 41 must be spaced at the same distance from the respective working electrodes 42 and 43 and have an area above 1.5 times larger than the working electrodes 42 and 43.

In the electrode systems shown in FIGS. 7a and 7b, the slit 71 formed at the cover 70 extends to above the reference electrode 41 and the working electrodes 42 and 43.

Figure 7C:
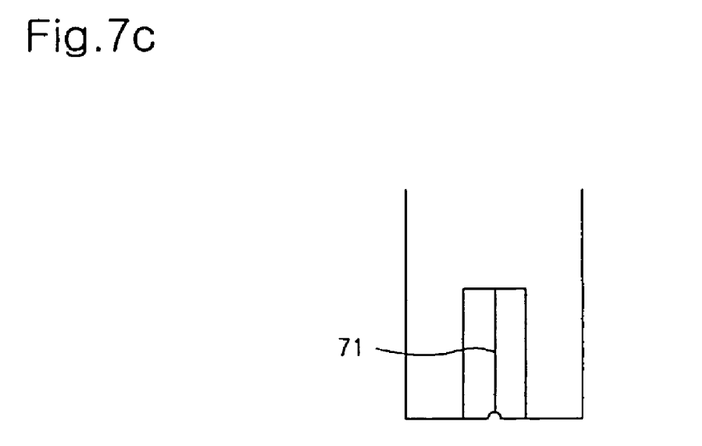
Figure 7D:
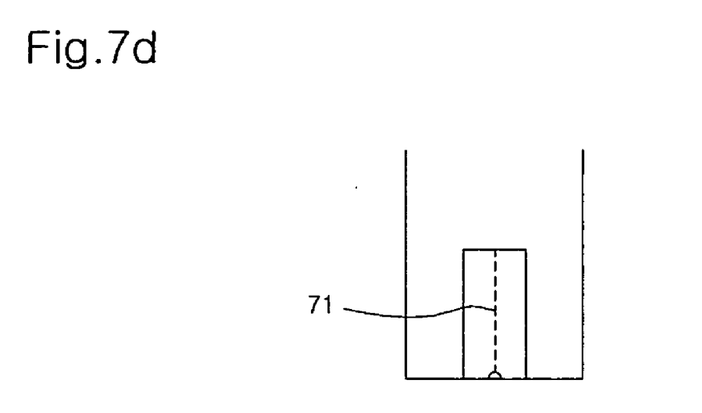
Figure 7E:
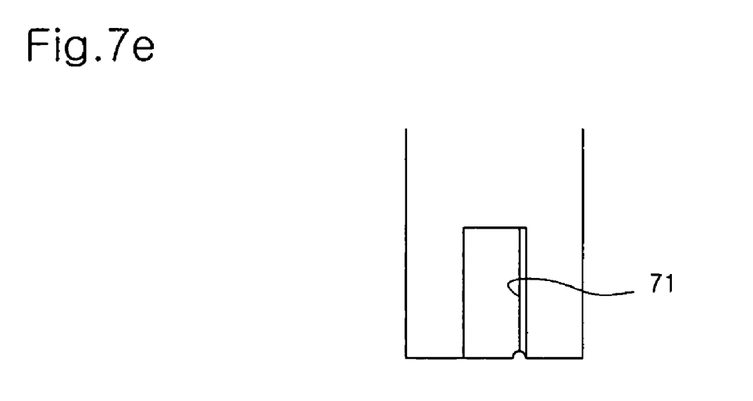

FIGS. 7c to 7e are diagrams showing various positions of the slit 71 formed at the cover 70. For example, FIG. 7c shows the slit 71 formed along a length direction of the cover 70, FIG. 7d shows a plurality of slits 71 formed at the center of the cover 70, each slit being spaced at a predetermined interval, and FIG. 7e shows the slit 71 formed along the right side of the cover 70. All slits 71 shown in FIGS. 7c to 7e extend to above the electrodes 41, 42 and 43 arranged on the base plate 20, thereby stably introducing the biological sample into the upper portion of the electrodes 41, 42 and 43.

Operation of a glucose sensor as an example of the biosensor according to the embodiment of the present invention will be explained below.

Referring to FIG. 3a, after the curved groove 72 of the glucose sensor is contacted with a blood sample, the blood sample is introduced into the sample introduction port 61 by virtue of capillary phenomenon and simultaneously air existing in the sample receiving space 62 is vented through the slit 71 formed at the cover 70. Subsequently, the blood sample is introduced into the first working electrode 43, the reference electrode 41 and the second working electrode 42 through the sample receiving space 62, and the blood sample is then impregnated into the enzyme reaction layer 80. Glucose contained in the blood sample enzymatically reacts with GOD, so that it is oxidized and simultaneously the GOD is reduced. The reduced GOD reacts with the electron acceptor and is reoxidized, after which the reoxidized GOD reacts with other glucose not yet oxidized. The reduced electron acceptor migrates to the surface of the electrode, to which a voltage is applied, and then loses electrons at the surface to be electrochemically reoxidized. Thereafter, the electron acceptor continuously takes part in the above reaction. The current generated during the oxidation of the electron acceptor is proportional to the concentration of glucose in the blood sample. Accordingly, the concentration of glucose in the blood sample can be more accurately and quantitatively obtained by measuring the amounts of current flowing in the first working electrode 43 and the reference electrode 41, and the second working electrode 42 and the reference electrode 41, respectively, and averaging the measured values.

To facilitate introduction of sample into the biosensor, the biosensor according to the present invention has the slit 71 formed at the cover, instead of an air hole. Accordingly, the biosensor according to the present invention can provide simplicity and convenience in handling the biosensor. In addition, since the slit 71 extends from one end of the cover 70 to above the electrodes, the sample can be rapidly introduced into the electrodes.

INDUSTRIAL APPLICABILITY

As described above, since the biosensor according to the present invention has an air-venting slit extending from one end of a cover to above the electrodes, a biological sample can be rapidly introduced. In addition, measurement errors caused by the biosensor can be minimized by measuring the amounts of current flowing in the two electrodes and one reference electrode, and averaging the measured values. Furthermore, since the biosensor according to the present invention does not include a separate air hole for facilitate introduction of a sample into the biosensor, it can provide simplicity and convenience in handling the biosensor.

While the present invention has been described with regard to preferred embodiments thereof, the description is for illustrative purposes only and is not to be construed as limiting the scope of the invention. Various modifications and changes may be made by those skilled in the art without departing from the true scope of the invention as defined by the appended claims.

The invention claimed is:

1. A biosensor comprising:
   an electrically insulating base plate;
   a plurality of lead terminals formed on the base plate;
   a plurality of lead wires connected to the lead terminals, respectively;
   an electrode system including two working electrodes and one reference electrode connected to the lead wires, respectively;
   an insulating layer that insulates the electrodes;
   an enzyme reaction layer formed on the insulating layer and the electrodes;
   a spacer formed on the enzyme reaction layer so as to ensure a sufficient space to receive a sample; and
   a cover formed on the spacer,
   wherein the spacer has a sample introduction port opened at one side of the spacer, and the cover has at least one slit that vents air existing in a sample receiving space defined by the spacer and the cover, the slit extending to above the electrodes from one end of the cover.

2. The biosensor as set forth in claim 1, further including a curved groove formed at one end of the cover toward the electrodes, the slit being formed from a certain position of the curved groove with a predetermined length.

3. The biosensor as set forth in claim 2, wherein the slit is a plurality of slits spaced at a predetermined interval along a length direction.

4. The biosensor as set forth in claim 2, wherein the respective working electrodes have the same electrical resistance and area, and the reference electrode is spaced at the same distance from the respective working electrodes.

5. The biosensor as set forth in claim 4, wherein the reference electrode has an area more than 1.5 times larger than the working electrodes.

6. The biosensor as set forth in claim 1, wherein the slit is a plurality of slits spaced at a predetermined interval along a length direction.

7. The biosensor as set forth in claim 1, wherein the respective working electrodes have the same electrical resistance and area, and the reference electrode is spaced at the same distance from the respective working electrodes.

8. The biosensor as set forth in claim 7, wherein the reference electrode has an area more than 1.5 times larger than the working electrodes.

9. The biosensor as set forth in claim 1, wherein when the sample receiving space is placed in a vertical direction, the reference electrode has an H-shape, and the respective working electrodes are arranged at the upper and lower portions of a horizontal axis of the reference electrode.

10. The biosensor as set forth in claim 9, wherein the respective working electrodes have the same electrical resistance and area, and the reference electrode is spaced at the same distance from the respective working electrodes.

11. The biosensor as set forth in claim 1, wherein when the sample receiving space is placed in a vertical direction, the reference electrode has an E-shape, and the respective working electrodes are arranged at the upper and lower portions of a horizontal axis, which is formed at the center of the reference electrode.

12. The biosensor as set forth in claim 11, wherein the respective working electrodes have the same electrical resistance and area, and the reference electrode is spaced at the same distance from the respective working electrodes.

* * * * *